United States Patent
Sun et al.

(10) Patent No.: US 9,617,653 B2
(45) Date of Patent: Apr. 11, 2017

(54) APPARATUS AND METHOD FOR FAST EVALUATION OF ELECTROPLATING FORMULATION PERFORMANCE IN MICROVIA FILLING

(71) Applicant: Hong Kong Applied Science and Technology Research Institute Company Limited, Hong Kong (HK)

(72) Inventors: Yaofeng Sun, Hong Kong (HK); Minghui Gao, Hong Kong (HK); Shu Kin Yau, Hong Kong (HK); Min Gao, Hong Kong (HK)

(73) Assignee: Hong Kong Applied Science and Technology Research Institute Company Limited, Hong Kong Science Park, Shatin, New Territories, Hong Kong (CN)

( * ) Notice: Subject to any disclaimer, the term of this patent is extended or adjusted under 35 U.S.C. 154(b) by 632 days.

(21) Appl. No.: 14/105,154

(22) Filed: Dec. 12, 2013

(65) Prior Publication Data

US 2015/0167195 A1 Jun. 18, 2015

(51) Int. Cl.
*C25D 17/12* (2006.01)
*C25D 21/12* (2006.01)
*G01N 27/403* (2006.01)
*C25D 5/18* (2006.01)

(52) U.S. Cl.
CPC ............ *C25D 21/12* (2013.01); *C25D 17/12* (2013.01); *G01N 27/403* (2013.01); *C25D 5/18* (2013.01)

(58) Field of Classification Search
CPC ....... C25D 17/12; C25D 21/12; G01N 27/403
See application file for complete search history.

(56) References Cited

U.S. PATENT DOCUMENTS

| | | | |
|---|---|---|---|
| 4,696,103 A | 9/1987 | Behl et al. | |
| 7,279,084 B2 | 10/2007 | Chalupa et al. | |
| 7,361,257 B2 | 4/2008 | Wang et al. | |
| 2004/0040842 A1 | 3/2004 | King et al. | |
| 2007/0215479 A1 | 9/2007 | Dow et al. | |

FOREIGN PATENT DOCUMENTS

JP 2008184681 A * 8/2008

* cited by examiner

*Primary Examiner* — Nicholas A Smith
(74) *Attorney, Agent, or Firm* — Spruson & Ferguson (Hong Kong) Limited (57) ABSTRACT

The presently claimed invention provides an electrochemical analytical apparatus and a method for evaluating performance of electroplating formulations of electrolyte solutions used for via filling. The electrochemical analytical apparatus comprises an electric power generating device, an electrical output signal measurement device, an electrochemical measurement device, and a motion generator. The electrochemical measurement device of the present invention comprises a supporting structure, a cavity, a cavity electrode, and a surface electrode. The electrical output signals of the cavity electrode and the surface electrode are measured during electroplating for calculating a filling performance value. The presently claimed invention provides an accurate, fast and cost effective method for evaluating performance of electroplating formulations, following with choosing the electroplating formulation of the highest FP value for actual microvia filling process.

20 Claims, 12 Drawing Sheets

APPARATUS AND METHOD FOR FAST EVALUATION OF ELECTROPLATING FORMULATION PERFORMANCE IN MICROVIA FILLING

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates generally to electrodeposition in via filling, and more particularly to apparatuses and methods for evaluating performance of electroplating formulations of electrolyte solutions in microvia filling.

BACKGROUND

Since the design rule for fabricating semiconductors has been greatly reduced in recent years, various technologies in semiconductor design and manufacturing have been highly developed. On the other hand, the market always has strong demand to manufacture cheaper, smaller, and lighter electronic products with better performance and more functions. The number of electronic device on a single chip is rapidly growing to meet this demand but the ability of two dimensional layouts in circuit design and fabrication to accommodate these demands has reached its limits.

Currently, three-dimensional integrated circuits (3D-ICs) provide breakthroughs to this bottleneck. A 3D-IC is a chip in which two or more layers of active electronic components are integrated both vertically and horizontally into a single integrated circuit. This is also referred to three-dimensional stacking, corresponding to a wafer level packaging technique in which specific components are fabricated on separate wafer platforms and then integrated onto a single wafer-scale or chip-scale package with through-silicon vias (TSVs) to provide electrical interconnections between the components inside the 3-D stack. TSVs provide a variety of advantages such as higher integration, better system performance, less power consumption, and lower parasitic losses. Consequently, many chip designers and manufacturers have shifted to this novel technique.

Electrodeposition is a frequently-used method to deposit different conductive metals into vias for forming electrical connections. Nevertheless, voids, insufficient filling, and non-uniform deposit are frequently found during via filling through electroplating, and such defects generate adverse effects to the devices.

In general, there are many parameters dictating the quality of vias including plating bath, via geometry, and additives used. In addition, the concentration and type of additives, via shape, aspect ratio (depth/width), current loading, and deposition time are frequently studied so as to optimize the electrodeposition process.

A traditional approach for investigating how the abovementioned parameters affect the process is through experiments. Vias in wafers are firstly electroplated under different parametric values and the processed wafers are cut for examining the cross section of the vias by an optical or a scanning electron microscope. In general, the time for depositing metal into vias takes about one hour. Then, the time for preparing the cross section of the vias, following with examination by a microscope is around 2-3 hours. Although investigating through experiments is able to provide solid results but this process for fabricating and characterizing the vias is extremely time consuming. For instance, if there are six process parameters to be studied and adjusted in a process, it may induce more than several hundreds of experiments because of the possible permutations of parameters, making such approach practically unfeasible.

For solving the abovementioned problems, computer simulation is deployed to simulate the electroplating process for determining the suitable process window of process parameters. For example, U.S. Pat. No. 7,279,084 discloses an electroplating method, which uses a computer to generate a model for calculating the current ratio between an inner anode and outer anode.

Nevertheless, accuracy of computer simulation is always a major concern. More consideration factors and more detailed models can be used to enhance accuracy of a computer simulation. However, the time and computing resources needed for running such computer simulation will increase enormously at the same time. Furthermore, in some cases, a wrong assumption or value used in the computer simulation may generate significant errors leading to useless simulation results for use in manufacturing.

Therefore, there is an unmet need to provide an accurate, fast, and cost effective method for evaluating performance of electroplating formulation of electrolyte solution used for via filling.

SUMMARY

Accordingly, it is a first aspect of the presently claimed invention to provide an electrochemical analytical apparatus for evaluating performance of electroplating formulation of electrolyte solution used for via filling.

In accordance with an embodiment of the presently claimed invention, an electrochemical analytical apparatus for evaluating performance of electroplating formulation of electrolyte solution used for via filling comprises an electric power generating device, an electrical output signal measurement device, an electrochemical measurement device, and a motion generator.

The electrochemical measurement device comprises: a supporting structure, comprising a measurement surface used for contacting with the electrolyte solution; a cavity, located inside the supporting structure, and comprising a top cavity opening and a bottom cavity opening, wherein the top cavity opening is located on the measurement surface of the supporting structure, and allows the electrolyte solution to flow into the cavity; a cavity electrode, located inside the supporting structure, wherein the cavity electrode comprises a cavity electrolytic surface, which is in contact with the bottom cavity opening, and is used for being electroplated by the electrolyte solution; and a surface electrode, located inside the supporting structure, wherein the surface electrode comprises a top electrolytic surface, which is located on the measurement surface of the supporting structure, and is used for being electroplated through the electrolyte solution. The surface electrode is electrically isolated from the cavity electrode by the supporting structure.

The motion generator is used for generating relative motion between the electrochemical measurement device and the electrolyte solution. The electric power generating device is electrically connected to the cavity electrode and provides a first electric loading to the cavity electrode for electroplating on the cavity electrolytic surface. Also the electric power generating device is electrically connected to the surface electrode and provides a second electric loading to the surface electrode for electroplating on the top electrolytic surface.

The electrical output signal measurement device is electrically connected to the cavity electrode and measures an electrical output signal of the cavity electrode. Also the electrical output signal measurement device is electrically connected to the surface electrode and measures an electrical output signal of the surface electrode. The measured electrical output signal of the cavity electrode and the measured electrical output signal of the surface electrode are used to evaluate the performance of the electroplating formulation of the electrolyte solution used for via filling by a filling performance (FP) value.

It is a second aspect of the presently claimed invention to provide the electrochemical measurement device to be used for evaluating performance of electroplating formulation of an electrolyte solution used for via filling.

In accordance with an embodiment of the presently claimed invention, the electrochemical measurement device comprises: a supporting structure, comprising a measurement surface used for contacting the electrolyte solution; a cavity, located inside the supporting structure, wherein the cavity comprises a top cavity opening and a bottom cavity opening, and wherein the top cavity opening is located on the measurement surface of the supporting structure, and allows the electrolyte solution to flow into the cavity; a cavity electrode, located inside the supporting structure, wherein the cavity electrode comprises a cavity electrolytic surface, which is in contact with the bottom cavity opening, and is used for being electroplated by the electrolyte solution; and a surface electrode, located inside the supporting structure, wherein the surface electrode comprises a top electrolytic surface, which is located on the measurement surface of the supporting structure, and is used for being electroplated through the electrolyte solution. The surface electrode is electrically isolated from the cavity electrode by the supporting structure. The supporting structure is cylindrical. The cavity is conical, and located along an axis of the supporting structure. The surface electrode has a ring shape that surrounds the cavity.

It is a third aspect of the presently claimed invention to provide a method for evaluating performance of electroplating formulation of an electrolyte solution used for via filling.

In accordance with an embodiment of the presently claimed invention, a method for evaluating performance of electroplating formulation of an electrolyte solution used for via filling comprises the steps of: providing an electrolyte solution with an electroplating formulation; inserting the electrochemical measurement device of the present invention into the electrolyte solution; generating relative motion between the electrochemical measurement device and the electrolyte solution; providing a first electric loading to the cavity electrode and a second electric loading to the surface electrode; electroplating metal on the cavity electrolytic surface and top electrolytic surface; measuring an electrical output signal of the cavity electrode and an electrical output signal of the surface electrode; and evaluating performance of the electroplating formulation of the electrolyte solution based on the electrical output signal of the cavity electrode and the electrical output signal of the surface electrode.

In accordance with another embodiment of the presently claimed invention, the method of present invention further comprises the steps of: calculating filling performance (FP) value based on the electrical output signal of the cavity electrode and the electrical output signal of the surface electrode; repeating the above steps using other electrolyte solutions of other electroplating formulations; and choosing at least one eletroplating formulation of relatively higher FP value for via filling, or choosing the eletroplating formulation of the highest FP value for via filling.

The presently claimed invention provides an accurate, fast and cost effective method for evaluating performance of electroplating formulation of an electrolyte solution used for via filling, further with choosing the suitable electroplating formulation of an electrolyte solution used for actual fabrication process. Comparing with the prior arts employing experimental approaches that often require hours for evaluating an electroplating formulation, only few minutes are needed for evaluation in the present invention. In addition, there is no need to use expensive wafers or substrate samples with micron vias for evaluation of electroplating formulation according to the apparatus and method of the present invention. Furthermore, use of plating bath and plating additives is highly reduced as well, thus substantially saving cost in finding the desirable electroplating formulation.

BRIEF DESCRIPTION OF THE DRAWINGS

Embodiments of the present invention are described in more detail hereinafter with reference to the drawings, in which.

DETAILED DESCRIPTION

In the following description, apparatuses and methods for evaluating performance of electroplating formulations of electrolyte solutions used for via filling are set forth as preferred examples. It will be apparent to those skilled in the art that modifications, including additions and/or substitutions may be made without departing from the scope and spirit of the invention. Specific details may be omitted so as not to obscure the invention; however, the disclosure is written to enable one skilled in the art to practice the teachings herein without undue experimentation.

Figure 1:
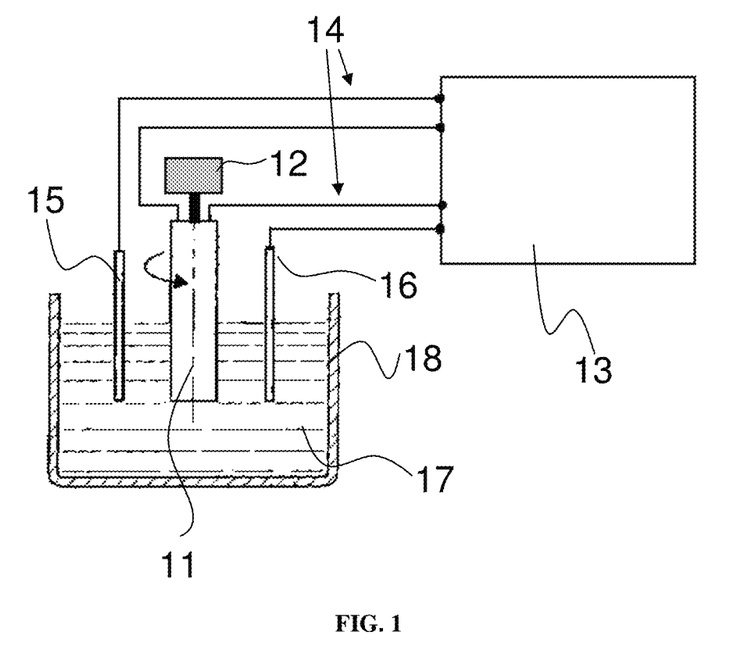
FIG. 1 shows a schematic diagram of an electrochemical analytical apparatus for evaluating performance of an electroplating formulation of an electrolyte solution used for via filling according to one embodiment of the presently claimed invention.

FIG. 1 shows a schematic diagram of an electrochemical analytical apparatus for evaluating performance of electroplating formulations of electrolyte solutions used for via filling. The electrochemical analytical apparatus comprises an electrochemical measurement device 11, a motion generator 12, an electrochemical analyzer 13, wires 14, a reference electrode 15, and a counter electrode 16.

The electrochemical measurement device 11 is connected to the motion generator 12, and is electrically connected to the electrochemical analyzer 13 by two of the electric wires 14. The reference electrode 15 and the counter electrode 16 are electrically connected to the electrochemical analyzer 13 by two of the electric wires 14 respectively. During via filling simulation, the electrochemical measurement device 11 is immersed into an electrolyte solution 17 contained in a container 18. The counter electrode 16 is used to make a connection to the electrolyte solution 17 so that a current/potential can be applied to the electrochemical measurement device 11. The reference electrode 15 has known and stable electrochemical potential, that is able to act as reference in measuring the electrochemical potential of the cavity electrode and the surface electrode. The electrochemical analyzer 13, serving for bi-channel power generation and electric signal measurement, comprises an electric power generating device an electrical output signal measurement device.

Figure 2A:
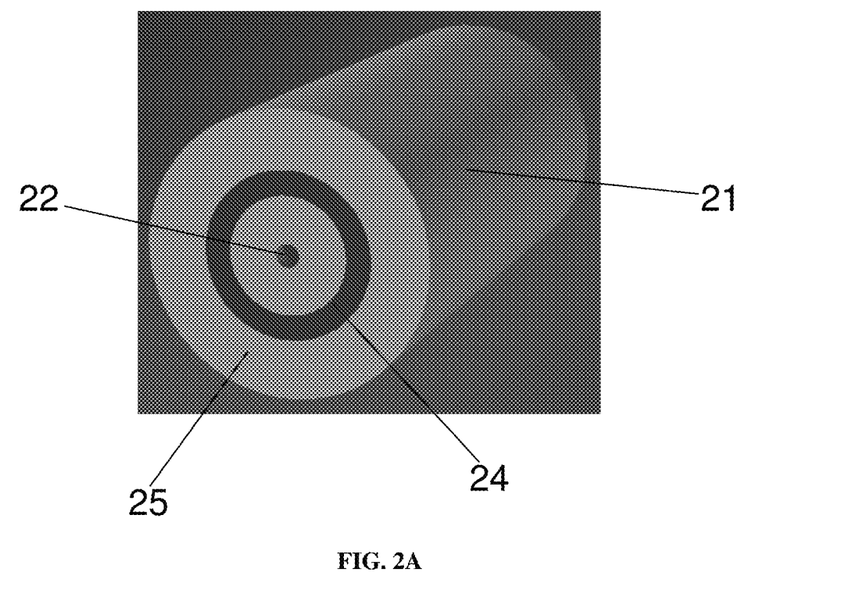
FIG. 2A is a perspective view of the electrochemical measurement device of the apparatus of FIG. 1.

FIG. 2A is a perspective view of the electrochemical measurement device 11. The electrochemical measurement device 11 comprises a supporting structure 21, a cavity 22, a cavity electrode (not shown in FIG. 2A), and a surface electrode 24. The supporting structure 21 is cylindrical, and made from electrically insulating material, and comprises a measurement surface 25 used for contacting the electrolyte solution 17 during measurement. The cavity 22 is conical, and located along an axis of the supporting structure 21. The surface electrode 24 has a ring shape that surrounds the cavity 22.

Figure 2B:
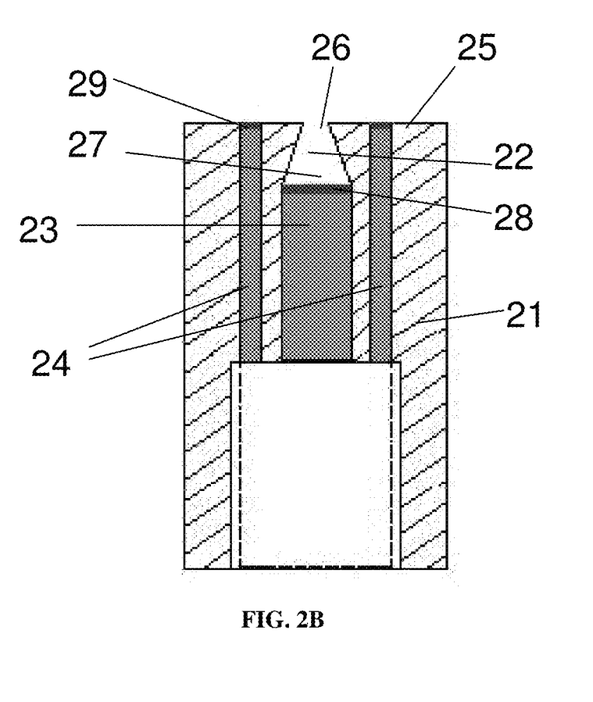
FIG. 2B is a cross-sectional diagram of the electrochemical measurement device of FIG. 2A.

FIG. 2B is a cross-sectional diagram of the electrochemical measurement device 11 of FIG. 2A. As shown in FIG. 2B, the supporting structure 21 fixes the positions of the cavity 22, the cavity electrode 23, and the surface electrode 24.

The cavity 22 is used for providing space for being electroplated. The cavity 22, located inside the supporting structure 21, comprises a top cavity opening 26 and a bottom cavity opening 27. The top cavity opening 26 is located on the measurement surface 25 of the supporting structure 21, and allows the electrolyte solution 17 to flow into the cavity 22. The bottom cavity opening 27 is in contact with the cavity electrode 23.

The cavity electrode 23 is located inside the supporting structure 21, and comprises a cavity electrolytic surface 28, which is located on the bottom cavity opening 27 and used for being electroplated by the electrolyte solution 17. The cavity electrode 23 is electrically connected to the electric power generating device 13 used for providing electric loading for electroplating metal on the cavity electrolytic surface 28 of the cavity electrode 23.

The surface electrode 24 is located inside the supporting structure 21, and comprises a top electrolytic surface 29, which is located on the measurement surface 25 of the supporting structure 13, and used for being electroplated by the electrolyte solution 17. The cavity electrode 24 is electrically connected to electric power generating device 13 used for providing electric loading for electroplating metal on the top electrolytic surface 29 of the surface electrode 24. The cavity electrode 23 and the surface electrode 24 are electrically isolated from each other by the supporting structure 21.

The electric power generating device is electrically connected to the cavity electrode 23 and the surface electrode 24 through the electric wires 14 for providing them with electric loadings separately such that electric charges are generated and transferred to the cavity electrode 23 and the surface electrode 24 to reduce dissolved metal cations in the electrolyte solution thereby depositing metal on the cavity electrolytic surface 28 and the top electrolytic surface 29.

The electric power generating device can operate at different operation modes to provide different electric loadings. For example, the electric loading is a constant potential for a potentiostatic loading mode, a constant current for a galvanostatic loading mode, a cyclic triangular waveform potential for a cyclic voltammetric stripping (CVS) loading mode, or a cyclic rectangular waveform potential for a cyclic pulse voltammetric stripping (CPVS) loading mode. Accordingly, the electric power generating device can be a galvanostat, or a potentiostat.

The motion generator 12 is used for generating relative motion between the electrochemical measurement device 11 and the electrolyte solution 17 to create flow of the electrolyte solution 17. Accordingly, the motion generator 12 is a rotational motor connected to the electrochemical measurement device 11 for rotating the electrochemical measurement device 11.

The electrical output signal measurement device is electrically connected to the cavity electrode 23 through the electric wires 14 for measuring the electrical output signal of the cavity electrode 23 during electroplating, and is electrically connected to the surface electrode 24 through the electric wires 14 for measuring the electrical output signal of the surface electrode 24 during electroplating. The electrical output signal of the cavity electrode and the electrical output signal of the surface electrode can be current density, potential, or electric charge. The electrical output signal measurement device can be a voltmeter, an ammeter, or a charge meter. The electrical output signal of the cavity electrode 23 and the electrical output signal of the surface electrode 24 are used to evaluate the performance of the electroplating formulation of the electrolyte solution 17 used for via filling.

Figure 2C:
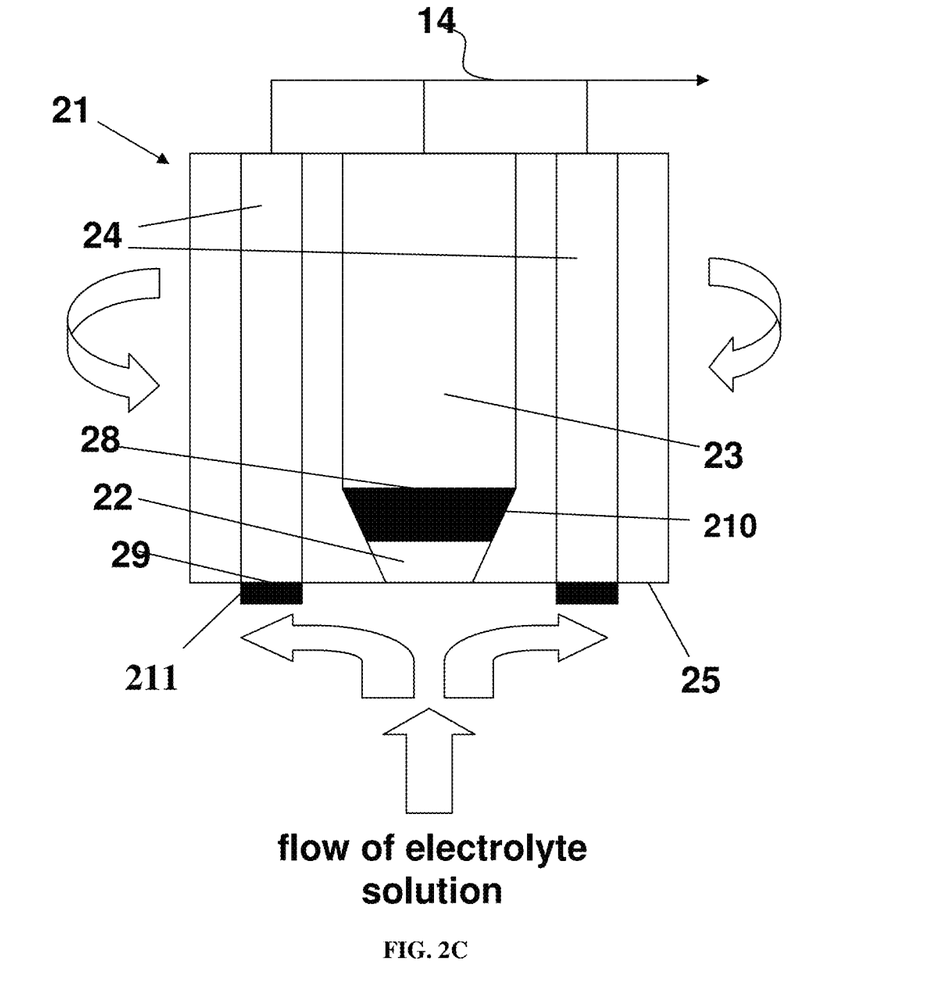
FIG. 2C is a cross-sectional diagram of an electrochemical measurement device during electrical output signal measurement according to one embodiment of the presently claimed invention.

FIG. 2C shows a cross-sectional diagram of an electrochemical measurement device during electrical output signal measurement according to one embodiment of the presently claimed invention. The supporting structure 21 is rotated by a rotational motor (not shown in FIG. 2C). The electrolyte solution flows into the cavity 22, or pass through the measurement surface 25 of the supporting structure 21. Metals 210 and 211 are electroplated on the cavity electrolytic surface 28, and the top electrolytic surface 29 respectively. Current from the cavity electrode 23 and current from the surface electrode 24 are measured separately by the electrical output signal measurement device through the electric wires 14.

According to various embodiments of the presently claimed invention, the performance of an electroplating formulation of an electrolyte solution used for via filling is evaluated by a filling performance (FP) value calculated by the electrical output signal of the cavity electrode and the electrical output signal of the surface electrode.

Figure 3:
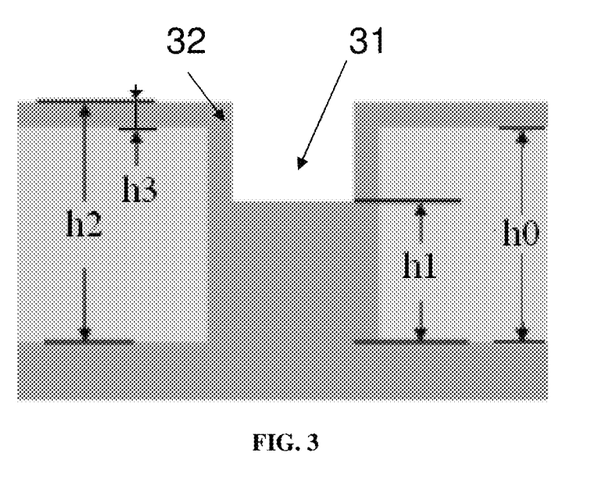
FIG. 3 is a cross-sectional diagram showing a via deposited with metal according to one embodiment of the presently claimed invention.

FIG. 3 is a schematic diagram showing a via deposited with metal used for deriving the FP value. As shown in FIG. 3, h0 denotes a via depth of a via 31, h1 denotes the height of metal 32 deposited inside the via 31, h2 denotes the via depth plus the height of metal 32 deposited on the top of the via, and h3 denotes the height of the metal 32 deposited on the top of the via. A ratio between h1 and h2 is a suitable parameter to evaluate the via filling performance. When h1 is closer to h2, the via is closer to be fully filled, meaning that the higher the ratio is, the better the via filling is. Accordingly, the FP value is derived from the below equation under a potentiostatic loading mode:

$$\frac{h1}{h2} = \frac{h1}{h0+h3} \propto \frac{h1}{h3} \propto \frac{i_{cavity}}{i_{surface}}$$

where $i_{cavity}$ denotes current density of the cavity electrode, and $i_{surface}$ denotes current density of the surface electrode.

h1 is proportional to $i_{cavity}$, and the h3 is proportional to $i_{surface}$ since deposition thickness (S) is proportional to the current (i) as shown by the below equation:

$$\frac{dS}{dt} = \frac{M_w}{\rho} \frac{i}{nF}$$

where $M_w$ denotes molecular weight of metal, $\rho$ denotes mass density of metal, n denotes valence of metal ion, and F denotes Faraday's constant.

Thus, the FP value is calculated as follows:

$$FP\ value = \frac{i_{cavity}}{i_{surface}}$$

With respect to a galvanostatic loading mode, the FP value is calculated as follows:

$$FP\ value = \eta_{surface} - \eta_{cavity}$$

where $\eta_{cavity}$ denotes potential of the cavity electrode, and $\eta_{surface}$ denotes potential of the surface electrode.

With respect to a CVS or a CPVS loading mode, the FP value is calculated as follows:

$$FP\ value = \frac{Q_{cavity}}{Q_{surface}}$$

where $Q_{cavity}$ denotes electric charge of the cavity electrode, and $Q_{surface}$ denotes electric charge of the surface electrode.

After acquiring FP values from various electroplating formulations of electrolyte solutions, the electroplating formulation of the highest FP value is chosen for actual via filling in wafer scale. Alternatively, the electroplating formulations of relatively higher FP values can also be chosen.

Generally, electroplating formulations of electrolyte solutions comprise the type and concentration of metal ion, and plating additives including suppressor, accelerator, and leveler, which are the major components for the quality of via filling. The apparatus of the present invention is able to find out suitable type and concentration of metal ion, and plating additives for actual wafer fabrication within a short period of time and in a cost effective way.

The design of the electrochemical measurement device of the present invention can be varied according to various applications. The supporting structure can be conical, cylindrical, rectangular, pyramidal, or in any other shapes. Similarly, the cavity can be conical, cylindrical, rectangular, pyramidal, or in any other shapes. The top cavity opening and the bottom cavity opening can be square, circular, triangular or in any other shape.

Figure 4A:
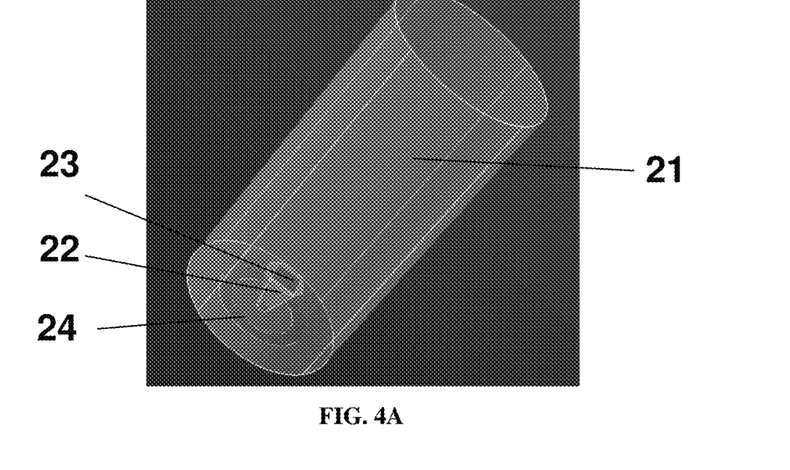
FIG. 4A-E show a first, a second, a third, a fourth, and a fifth exemplary embodiments of the electrochemical measurement device of the presently claimed invention.

According to a first exemplary embodiment of the electrochemical measurement device as shown in FIG. 4A, the supporting structure 21 is cylindrical, the cavity 22 is located at an axis of the supporting structure 21, the cavity 22 is conical with the top cavity opening smaller than the bottom cavity opening. The cavity electrode 23 is quadrilateral. The surface electrode 24 is ring-shaped and surrounds the cavity 22.

Figure 4B:
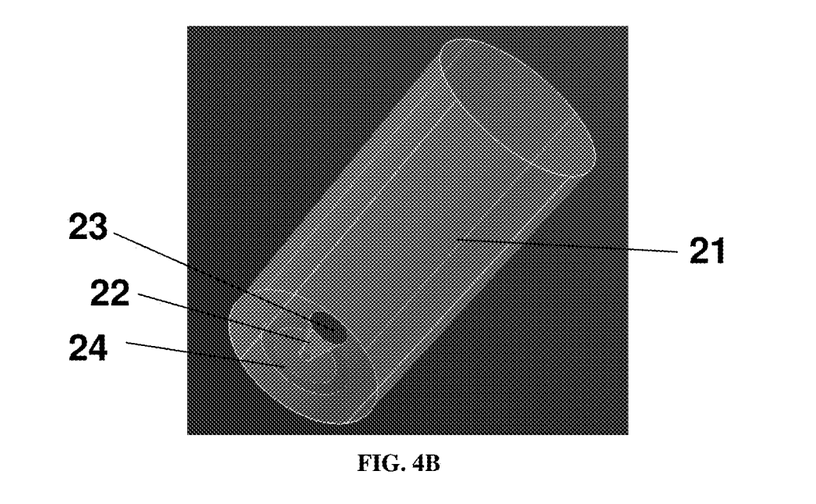

According to a second exemplary embodiment of the electrochemical measurement device as shown in FIG. 4B, the supporting structure 21 is cylindrical, the cavity 22 is located at an axis of the supporting structure 21, the cavity 22 is conical with the top cavity opening smaller than the bottom cavity opening. The cavity electrode 23 is cylindrical. The surface electrode 24 is ring-shaped and surrounds the cavity 22. The material of the cavity electrode 22 is different from that of the surface electrode 23.

Figure 4C:
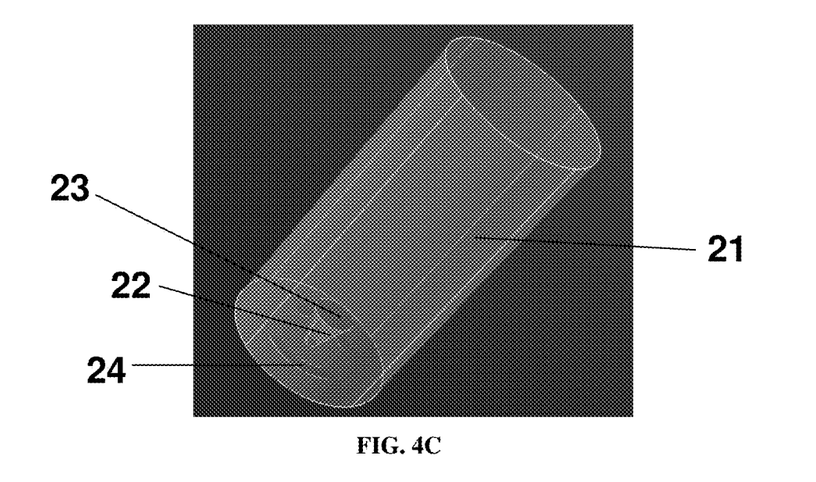

According to a third exemplary embodiment of the electrochemical measurement device as shown in FIG. 4C, the supporting structure 21 is cylindrical, the cavity 22 is located at an axis of the supporting structure 21, the cavity 22 is conical with the top cavity opening smaller than the bottom cavity opening. The cavity electrode 23 is cylindrical. The surface electrode 24 is in partial ring shape and partially surrounds the cavity 22.

Figure 4D:
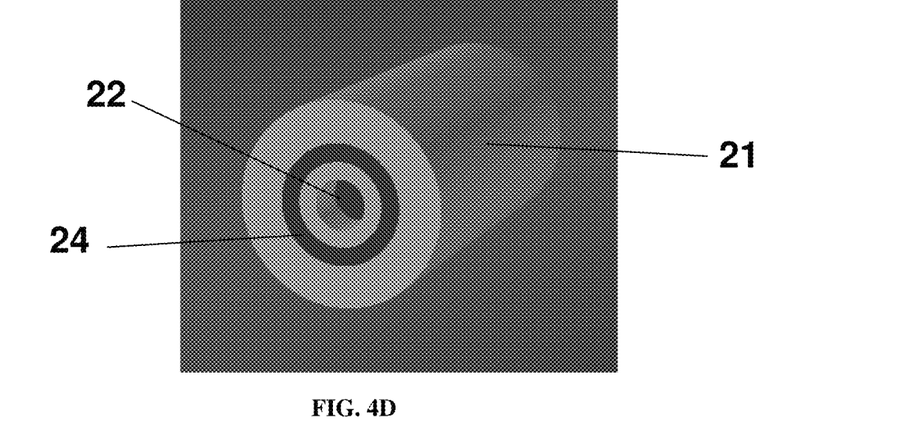

According to a fourth exemplary embodiment of the electrochemical measurement device as shown in FIG. 4D, the supporting structure 21 is cylindrical, the cavity 22 is located at an axis of the supporting structure 21, the cavity 22 is cylindrical with the top cavity opening having the same diameter as the bottom cavity opening. The cavity electrode 23 is cylindrical. The surface electrode 24 is in ring shape and surrounds the cavity 22.

Figure 4E:
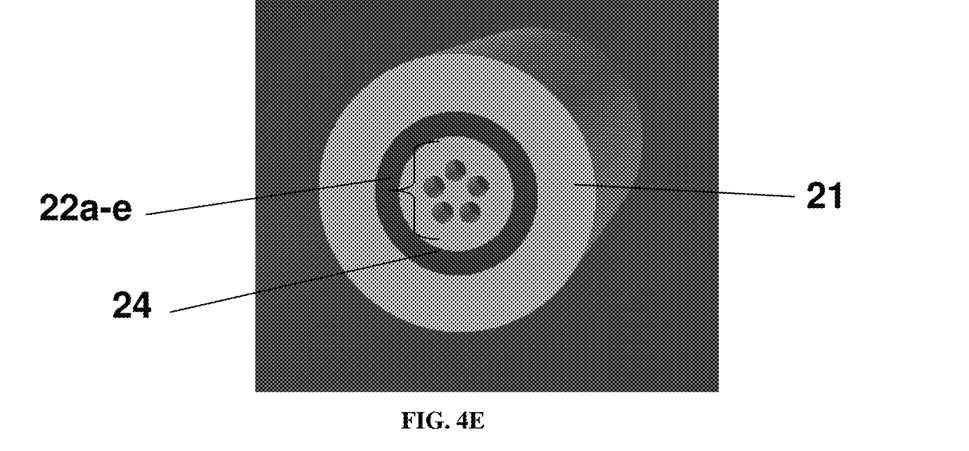

Apart from the single cavity used, multiple cavities can also be employed. According to a fifth example of the electrochemical measurement device as shown in FIG. 4E, the supporting structure 21 is cylindrical, and five cavities 22a-e are located around an axis of the supporting structure 21. The surface electrode 24 is ring-shaped and surrounds the five cavities 22a-e. Accordingly, the structures of the cavities 22a-e can be same or different.

Preferably, the top cavity opening is smaller than the bottom cavity opening. Preferably, the top cavity opening and the bottom cavity opening are circular, and a ratio of diameter between the top cavity opening and the bottom cavity opening is in the range from 1:6 to 1:1 that is able to provide more accurate via filling simulation results.

According to various embodiments of the present invention, the top cavity opening is in the range from 1 to 3 mm in diameter, the bottom cavity opening is in the range from 3 to 6 mm in diameter, and the depth of the cavity is in the range from 3 to 6 mm.

Accordingly, the motion generator of the present invention can comprise a magnetic stirrer and a magnetic bar. The magnetic stirrer is placed beneath the container of electrolyte solution, and the magnetic bar is immersed inside the electrolyte solution. The magnetic stirrer employs a rotating magnetic field to cause the stir bar to spin in the electrolyte solution, thus stirring the electrolyte solution.

Alternatively, the motion generator is a rotational motor connected to the container to cause the rotation of the container.

Preferably, the relative motion between the measurement unit and the electrolyte solution is a rotational motion at a rotating axis. The rotation speed of the motion generator is in the range from 50 rpm to 5000 rpm.

According to one embodiment of the present invention, two electric power generating devices are used to provide electrical loadings to the cavity electrode and the surface electrode respectively.

According to another embodiment of the present invention, two electrical output signal measurement devices are used to connect to the cavity electrode and the surface electrode respectively for measuring the electrical output signal of the cavity electrode and the electrical output signal of the surface electrode.

According to an embodiment of the present invention, the apparatus of the present invention further comprises one or more computer processors for calculating the FP value based on the measured electrical output signals of the cavity electrode and the surface electrode.

Figure 5:
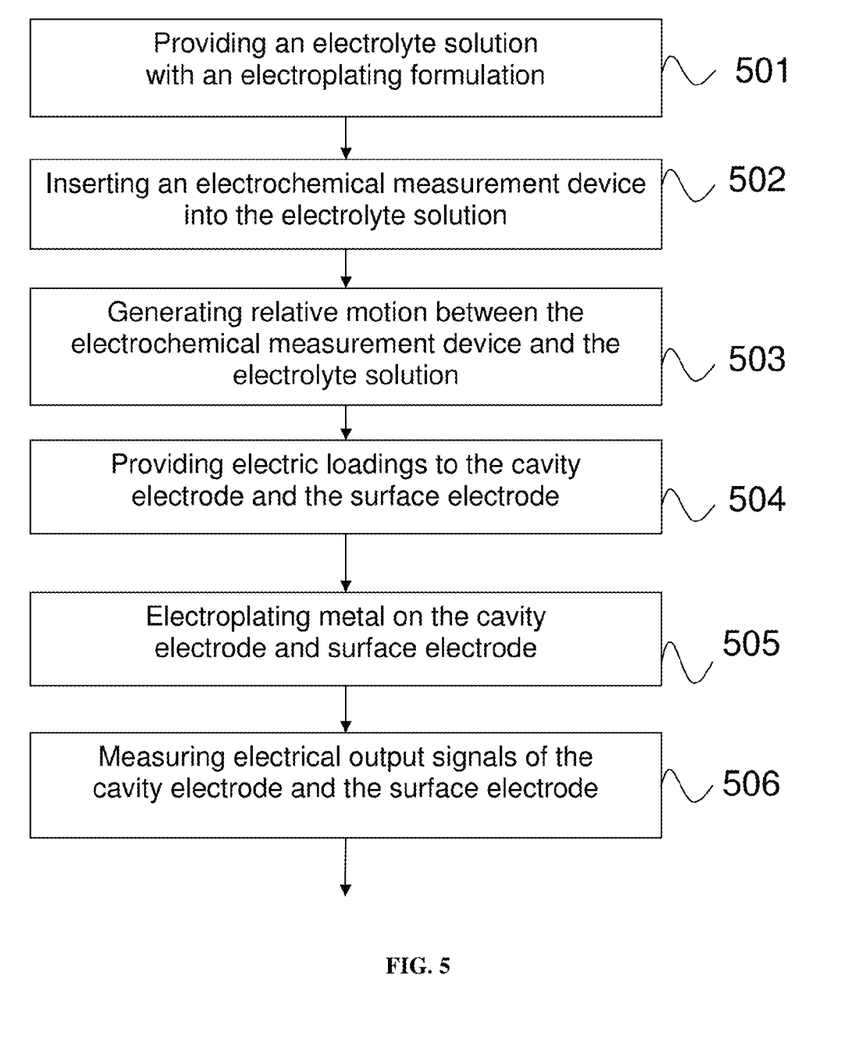
FIG. 5 shows a process flow diagram illustrating the steps of evaluating performance of electroplating formulations of electrolyte solutions used for via filling according to one embodiment of the presently claimed invention.

FIG. 5 shows a process flow diagram illustrating the steps of evaluating performance of electroplating formulations of electrolyte solutions used for via filling according to one embodiment of the presently claimed invention. In step 501, an electrolyte solution with an electroplating formulation is provided. In step 502, the electrochemical measurement device of the present invention is inserted into the electrolyte solution. The measurement surface of the electrochemical measurement device is immersed in the electrolyte solution. In step 503, relative motion between the electrochemical measurement device and the electrolyte solution is generated. In step 504, electric loadings are provided to the cavity electrode and the surface electrode for electroplating respectively. In step 505, the cavity electrolytic surface of the cavity electrode and the top electrolytic surface of the surface electrode are electroplated with metal. In step 506, an electrical output signal of the cavity electrode and an electrical output signal of the surface electrode are measured respectively during electroplating. In step 507, a filling performance (FP) value is calculated based on the electrical output signal of the cavity electrode and the electrical output signal of the surface electrode for evaluating performance of the electroplating formulation of the electrolyte solution. In step 508, the steps 501-507 are repeated with other electrolyte solutions having other electroplating formulations. In step 509, the electroplating formulation of the highest FP value is chosen for actual via filling.

In step 504, the electric loadings can be constant potential for a potentiostatic loading mode, constant current for a galvanostatic loading mode, cyclic triangular waveform potential for a cyclic voltammetric stripping (CVS) loading mode, or cyclic rectangular waveform potential for a cyclic pulse voltammetric stripping (CPVS) loading mode.

In step 506, the electrical output signals of the cavity electrode and the surface electrode can be current density, potential, or electric charge. In step 507, the FP value is calculated by one of the following equations:

$$FP \text{ value} = \frac{i_{cavity}}{i_{surface}}$$

where $i_{cavity}$ is current density of the cavity electrode, and $i_{surface}$ is current density of the surface electrode;

FP value=$\eta_{surface} - \eta_{cavity}$ where $\eta_{cavity}$ is potential of the cavity electrode, and $\eta_{surface}$ is potential of the surface electrode; and $$FP \text{ value} = \frac{Q_{cavity}}{Q_{surface}}$$

where $Q_{cavity}$ is electric charge of the cavity electrode, and $Q_{surface}$ is electric charge of the surface electrode.

Alternatively, one or more electroplating formulations having relatively higher FP values are chosen for actual via filling in step 509.

An experiment was conducted to evaluate correlation between the FP value and the actual microvia filling profile to prove whether the FP value was accurate enough to reflect microvia filling performance. The experiment included sample testing and experimental testing.

For the sample testing, three electrolyte solutions with three concentrations of plating leveler including 8 ml/L, 15 ml/L and 30 ml/L were used. Plating suppressor of 10 ml/L, and plating accelerator of 0.75 ml/L were used. The electrochemical measurement device comprises a cavity with a top cavity opening of Ø1 mm, a bottom cavity opening of Ø3 mm, and a depth of 3 mm. The rotation speed is 100 rpm. The electrolyte solutions were tested by the apparatus of the present invention at the potentiostatic loading mode. Current densities for each plating leveler concentration with respect to the cavity electrode and the surface electrode were measured during electroplating for calculating the corresponding FP values.

For the experimental testing, wafers with microvias were used to be electroplated with metal by the abovementioned electrolyte solutions. The microvias used for testing were in diameter of 35 µm and depth of 40 µm. The deposition time was 20 mins. After electroplating, the wafers were cut to examine their microvia filling profiles.

Figure 6A:
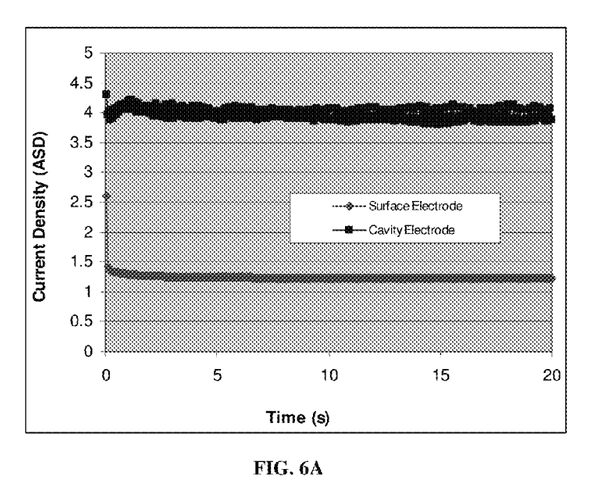
FIG. 6A-C are graphs showing relationship between current density and time with respect to the plating leveler concentrations of 8 ml/L, 15 ml/L and 30 ml/L according to one embodiment of the presently claimed invention.
Figure 6B:
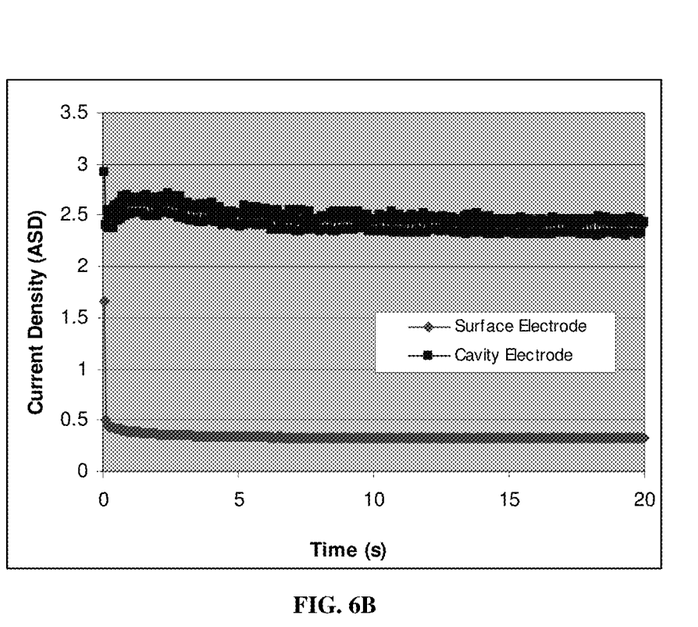
Figure 6C:
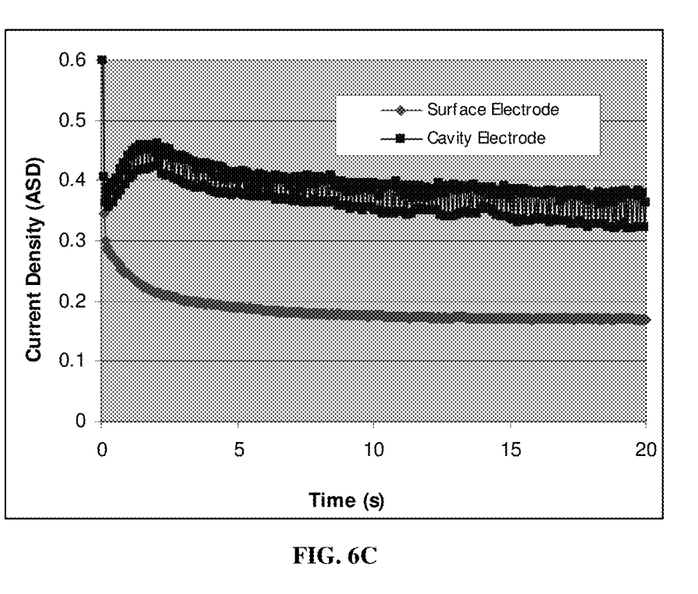

FIG. 6A-C are graphs showing the results of the sample testing. The relationship between current density and time is plotted in the graphs at the plating leveler concentrations of 8 ml/L, 15 ml/L and 30 ml/L. The upper line in the graph corresponds to the current density of the cavity electrode, and the lower line in the graph corresponds to the current density of the surface electrode. After calculation based on the values of the current density of the cavity electrode and the surface electrode, the FP values are 3.18, 7.21 and 2.04 with respect to the plating leveler concentrations of 8 ml/L, 15 ml/L and 30 ml/L.

Figure 7A:
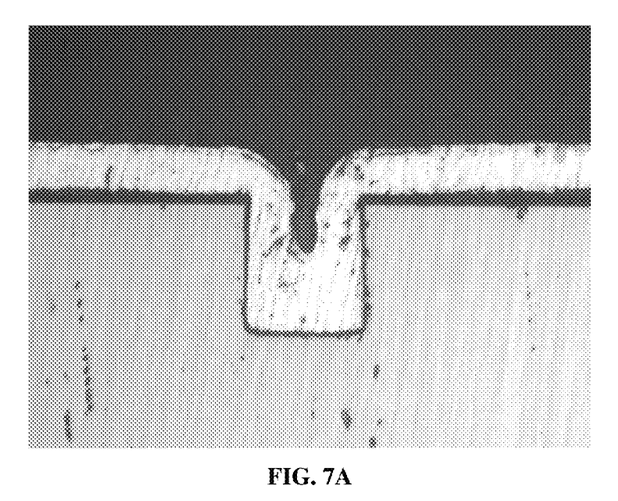
FIG. 7A-C are photos showing cross sections of the microvia filling profiles with respect to the plating leveler concentrations of 8 ml/L, 15 ml/L and 30 ml/L.
Figure 7B:
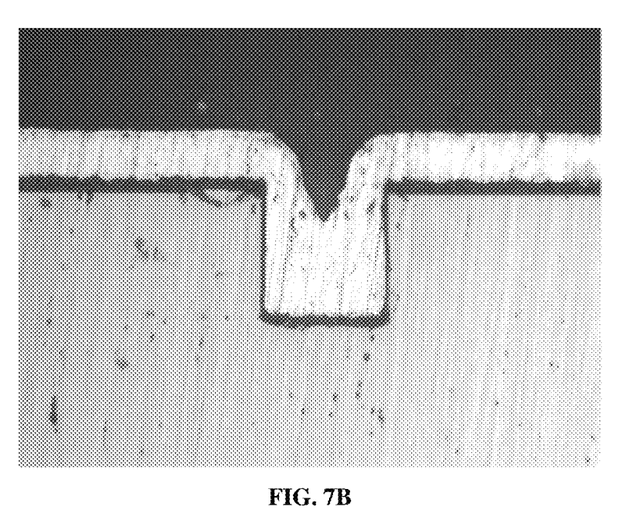
Figure 7C:
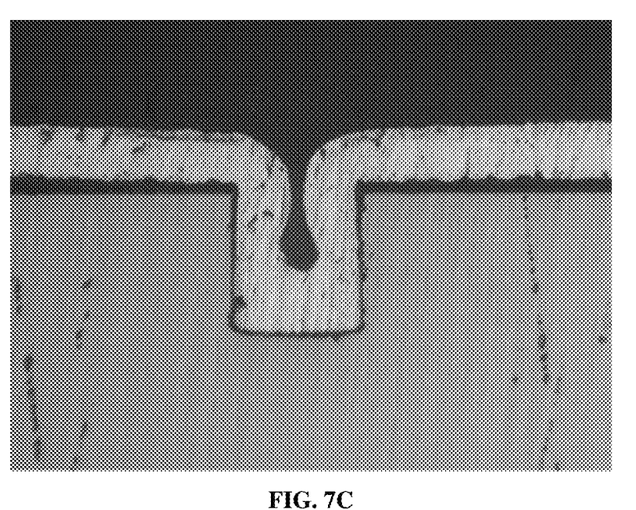

FIG. 7A-C are photos showing cross sections of the micovia filling profiles with respect to the plating leveler concentrations of 8 ml/L, 15 ml/L and 30 ml/L respectively. Through comparing among the microvia filling profiles of FIG. 7A-C, the microvia filling profile of FIG. 7B is mostly filled among others, and the corresponding FP value is 7.21, being the highest among the three. Similarly, the microvia shown in FIG. 7C is least filled among others, and the corresponding FP value is 2.04, being the lowest among others. The results prove that an electroplating formulation with higher FP value leads to have better microvia filling performance comparing with the one with lower FP value. Consequently, the sample testing conducted by the electrochemical analytical apparatus and method of the present invention is able to find out suitable electroplating formulations.

In consequence, the apparatuses and the methods of the present invention are able to provide a fast and cost effective method for evaluating performance of electroplating formulations of electrolyte solutions used for via filling.

The embodiments disclosed herein may be implemented using general purpose or specialized computing devices, computer processors, or electronic circuitries including but not limited to digital signal processors (DSP), application specific integrated circuits (ASIC), field programmable gate arrays (FPGA), and other programmable logic devices configured or programmed according to the teachings of the present disclosure. Computer instructions or software codes running in the general purpose or specialized computing devices, computer processors, or programmable logic devices can readily be prepared by practitioners skilled in the software or electronic art based on the teachings of the present disclosure.

In some embodiments, the present invention includes computer storage media having computer instructions or software codes stored therein which can be used to program computers or microprocessors to perform any of the processes of the present invention. The storage media can include, but are not limited to, floppy disks, optical discs, Blu-ray Disc, DVD, CD-ROMs, and magneto-optical disks, ROMs, RAMs, flash memory devices, or any type of media or devices suitable for storing instructions, codes, and/or data.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

What is claimed is:

1. An electrochemical measurement device for evaluating performance of an electroplating formulation of an electrolyte solution used for via filling, comprising:
   at least one supporting structure, comprising at least one measurement surface for contacting the electrolyte solution;
   at least one cavity, located at the supporting structure, and comprising a top cavity opening and a bottom cavity opening, wherein the top cavity opening is located on the measurement surface of the supporting structure, and allows the electrolyte solution to flow into the cavity;
   at least one cavity electrode, wherein the cavity electrode comprises at least one cavity electrolytic surface, which is in contact with the bottom cavity opening, and is used for being electroplated by the electrolyte solution; and
   at least one surface electrode, wherein the surface electrode comprises at least one top electrolytic surface, which is located on the measurement surface of the supporting structure, and is used for being electroplated by the electrolyte solution; and
   wherein the surface electrode is electrically isolated from the cavity electrode by the supporting structure.

2. The device of claim 1, wherein the supporting structure is cylindrical, the cavity is conical and located along an axis of the supporting structure, and the surface electrode has a ring shape surrounding the cavity.

3. The device of claim 1, wherein the cavity is cylindrical, or conical.

4. The device of claim 1, wherein the top cavity opening is smaller than the bottom cavity opening.

5. The device of claim 1, wherein the top cavity opening and the bottom cavity opening are circular, and a ratio of diameter between the top cavity opening and the bottom cavity opening is in the range from 1:6 to 1:1.

6. The device of claim 1, further comprising more than one cavity and more than one cavity electrode, and the cavities and the cavity electrodes are located substantially at the center of the measurement surface of the supporting structure.

7. The device of claim 1, wherein the surface electrode has a partial ring shape.

8. The device of claim 1, further comprising a motion generator for generating relative motion between the electrochemical measurement device and the electrolyte solution.

9. The device of claim 1, wherein the cavity electrode, and the surface electrode are formed with different electrode materials.

10. A method for evaluating performance of at least one electroplating formulation of at least one electrolyte solution used for via filling, comprising the steps of:
    providing an electrolyte solution with an electroplating formulation;
    inserting an electrochemical measurement device of claim 1 into the electrolyte solution;
    generating relative motion between the electrochemical measurement device and the electrolyte solution;
    measuring an electrical output signal of the cavity electrode and an electrical output signal of the surface electrode; and
    evaluating performance of the electroplating formulation of the electrolyte solution based on the electrical output signal of the cavity electrode and the electrical output signal of the surface electrode.

11. The method of claim 10, wherein the step of evaluating the performance of the electroplating formulation of the electrolyte solution further comprises:
    calculating filling performance (FP) value based on the electrical output signal of the cavity electrode and the electrical output signal of the surface electrode.

12. The method of claim 11, wherein the electrical output signal of the cavity electrode and the electrical output signal of the surface electrode are current density, potential, or electric charge, wherein the FP value is calculated by one of the following equations:

$$FP \text{ value} = \frac{i_{cavity}}{i_{surface}}$$

where $i_{cavity}$ is current density of the cavity electrode, and $i_{surface}$ is current density of the surface electrode;

$$FP \text{ value} = \eta_{surface} - \eta_{cavity}$$

where $\eta_{cavity}$ is potential of the cavity electrode, and $\eta_{surface}$ is potential of the surface electrode; and $$FP \text{ value} = \frac{Q_{cavity}}{Q_{surface}}$$

where $Q_{cavity}$ is electric charge of the cavity electrode, and $Q_{surface}$ is electric charge of the surface electrode.

13. The method of claim 11, further comprising:
repeating the above steps using other electrolyte solutions with other electroplating formulations; and
choosing at least one eletroplating formulation of relatively higher FP value for via filling, or choosing the eletroplating formulation of the highest FP value for via filling.

14. The method of claim 10, further comprising:
providing a first electric loading to the cavity electrode and a second electric loading to the surface electrode; and
electroplating metal on the cavity electrolytic surface and top electrolytic surface.

15. The method of claim 14, wherein the first electric loading and second electric loading are constant potential for a potentiostatic loading mode, constant current for a galvanostatic loading mode, cyclic triangular waveform potential for a cyclic voltammetric stripping (CVS) loading mode, or cyclic rectangular waveform potential for a cyclic pulse voltammetric stripping (CPVS) loading mode.

16. An electrochemical analytical apparatus for evaluating performance of an electroplating formulation of an electrolyte solution used for via filling, comprising:
at least one electric power generating device;
at least one electrical output signal measurement device;
at least one electrochemical measurement device, comprising:
at least one supporting structure, comprising at least one measurement surface used for contacting the electrolyte solution;
at least one cavity, located at the supporting structure, and comprising a top cavity opening and a bottom cavity opening, wherein the top cavity opening is located on the measurement surface of the supporting structure, and allows the electrolyte solution to flow into the cavity;
at least one cavity electrode, wherein the cavity electrode comprises at least one cavity electrolytic surface, which is in contact with the bottom cavity opening, and is used for being electroplated by the electrolyte solution; and
at least one surface electrode, wherein the surface electrode comprises at least one top electrolytic surface, which is located on the measurement surface of the supporting structure, and is used for being electroplated by the electrolyte solution, wherein the surface electrode is electrically isolated from the cavity electrode by the supporting structure;
at least one motion generator for generating relative motion between the electrochemical measurement device and the electrolyte solution;
wherein the electric power generating device is electrically connected to the cavity electrode and provides a first electric loading to the cavity electrode for electroplating on the cavity electrolytic surface, and the electric power generating device is electrically connected to the surface electrode and provides a second electric loading to the surface electrode for electroplating on the top electrolytic surface;
wherein the electrical output signal measurement device is electrically connected to the cavity electrode and used for measuring an electrical output signal of the cavity electrode during electroplating, and the electrical output signal measurement device is electrically connected to the surface electrode and used for measuring an electrical output signal of the surface electrode during electroplating; and
wherein the measured electrical output signal of the cavity electrode and the measured electrical output signal of the surface electrode are used to evaluate performance of the electroplating formulation of the electrolyte solution used for via filling.

17. The apparatus of claim 16, wherein the performance of the electroplating formulation of the electrolyte solution used for via filling is evaluated by a filling performance (FP) value calculated by the electrical output signal of the cavity electrode and the electrical output signal of the surface electrode.

18. The apparatus of claim 17, wherein the electrical output signal of the cavity electrode and the electrical output signal of the surface electrode are current density, potential, or electric charge, and wherein the FP value is calculated by one of the following equations:

$$FP \text{ value} = \frac{i_{cavity}}{i_{surface}}$$

where $i_{cavity}$ is current density of the cavity electrode, and $i_{surface}$ is current density of the surface electrode;

$$FP \text{ value} = \eta_{surface} - \eta_{cavity}$$

where $\eta_{cavity}$ is potential of the cavity electrode, and $\eta_{surface}$ is potential of the surface electrode; and $$FP \text{ value} = \frac{Q_{cavity}}{Q_{surface}}$$

where $Q_{cavity}$ is electric charge of the cavity electrode, and $Q_{surface}$ is electric charge of the surface electrode.

19. The apparatus of claim 16, wherein the supporting structure is cylindrical, the cavity is conical and located along an axis of the supporting structure, and the surface electrode has a ring shape surrounding the cavity.

20. The apparatus of claim 16, wherein the motion generator is a rotational motor connected to the supporting structure, or a container of the electrolyte solution.

* * * * *